(12) United States Patent
Cooper et al.

(10) Patent No.: US 10,579,747 B2
(45) Date of Patent: Mar. 3, 2020

(54) INJECTION OF SIMULATED SOURCES IN A SYSTEM OF NETWORKED SENSORS

(71) Applicant: Passport Systems, Inc., Billerica, MA (US)

(72) Inventors: Daniel A. Cooper, Acton, MA (US); James B. Costales, Winchester, MA (US); Krzysztof E. Kamieniecki, Acton, MA (US); Robert J. Ledoux, Harvard, MA (US); Jeffrey K. Thompson, Woburn, MA (US); Stephen E. Korbly, Acton, MA (US)

(73) Assignee: Passport Systems, Inc., Billerica, MA (US)

( * ) Notice: Subject to any disclaimer, the term of this patent is extended or adjusted under 35 U.S.C. 154(b) by 888 days.

(21) Appl. No.: 14/358,613

(22) PCT Filed: May 7, 2014

(86) PCT No.: PCT/US2014/037210
§ 371 (c)(1),
(2) Date: May 15, 2014

(87) PCT Pub. No.: WO2015/057264
PCT Pub. Date: Apr. 23, 2015

(65) Prior Publication Data
US 2015/0186566 A1    Jul. 2, 2015

Related U.S. Application Data

(60) Provisional application No. 61/891,636, filed on Oct. 16, 2013.

(51) Int. Cl.
*G06F 17/50* (2006.01)
*G06N 5/04* (2006.01)

(52) U.S. Cl.
CPC .......... *G06F 17/5009* (2013.01); *G06N 5/04* (2013.01)

(58) Field of Classification Search
CPC ... G06F 17/5009; G06F 19/3493; G06N 5/04; G08B 29/14
(Continued)

(56) References Cited

U.S. PATENT DOCUMENTS 4,910,149 A * 3/1990 Okube ............... G01T 1/04
250/370.07
4,973,913 A * 11/1990 Oda ................... G01T 1/17
250/369

(Continued)

FOREIGN PATENT DOCUMENTS

EP    2592611 A1 *  5/2013  ............ G09B 9/00
EP    2592611 A1     5/2013

OTHER PUBLICATIONS

Cui et al. ("Swarm-based Fuzzy Logic Control Mobile Sensor Network for Hazardous Contaminants Localization", IEEE, 2004, pp. 194-203, No. of pp. :10).*

(Continued)

*Primary Examiner* — Kamini S Shah
*Assistant Examiner* — Iftekhar A Khan
(74) *Attorney, Agent, or Firm* — Foley Hoag LLP; Rajesh Vallabh

(57) ABSTRACT

Methods and systems are disclosed for detecting a source (such as, e.g., radioactive and chemical sources) using a plurality of networked sensors communicating with a central processor over network. A method can involve injecting a simulated source in the system of networked sensors for use in operational training and/or testing.

36 Claims, 3 Drawing Sheets

(58) Field of Classification Search
USPC .......................................................... 703/21
See application file for complete search history.

(56) References Cited

U.S. PATENT DOCUMENTS

| | | | | |
|---|---|---|---|---|
| 5,142,559 | A * | 8/1992 | Wielopolski | A61B 6/08 250/492.3 |
| 5,304,065 | A * | 4/1994 | Hurst | G01T 1/16 250/370.07 |
| 5,722,835 | A * | 3/1998 | Pike | G01N 29/36 434/218 |
| 5,979,565 | A * | 11/1999 | Wicks | A62B 13/00 169/17 |
| 6,033,225 | A * | 3/2000 | Pike | G01N 29/36 434/218 |
| 6,293,861 | B1 * | 9/2001 | Berry | F24F 11/30 454/255 |
| 6,393,375 | B1 * | 5/2002 | Sivathanu | G01J 5/0014 250/339.01 |
| 6,531,701 | B2 * | 3/2003 | Chou | G01N 21/3504 250/339.08 |
| 6,946,644 | B2 * | 9/2005 | Wood | G01J 3/0254 250/216 |
| 7,194,395 | B2 * | 3/2007 | Genovese | G06Q 10/00 700/83 |
| 7,391,557 | B1 * | 6/2008 | Bruch | G01J 3/10 356/450 |
| 7,412,356 | B1 * | 8/2008 | Dzenitis | G16H 50/80 702/189 |
| 7,770,224 | B2 * | 8/2010 | Pellegrino | G08B 31/00 726/23 |
| 8,794,973 | B2 * | 8/2014 | Darois | G09B 9/00 434/218 |
| 8,827,714 | B2 * | 9/2014 | Goforth | G09B 19/00 434/219 |
| 9,165,475 | B2 * | 10/2015 | Ambrose | G09B 9/00 |
| 9,836,993 | B2 * | 12/2017 | Dunlop | G09B 19/00 |
| 10,260,948 | B2 * | 4/2019 | Hoeffner | G01N 21/538 |
| 2004/0002843 | A1 * | 1/2004 | Robarts | A63F 13/10 703/13 |
| 2004/0015336 | A1 * | 1/2004 | Kulesz | G08B 21/12 703/11 |
| 2004/0053421 | A1 * | 3/2004 | Nguyen | G01N 21/76 436/172 |
| 2004/0114130 | A1 * | 6/2004 | Nguyen | G01N 1/24 356/36 |
| 2004/0212388 | A1 * | 10/2004 | Baumann | G21K 5/02 324/762.01 |
| 2004/0215047 | A1 * | 10/2004 | Apple | A61B 17/68 600/3 |
| 2005/0118704 | A1 * | 6/2005 | Malobabic | G01N 1/14 435/287.1 |
| 2007/0015115 | A1 * | 1/2007 | Jones | F41A 33/00 434/11 |
| 2007/0090942 | A1 * | 4/2007 | Berry | G16H 50/80 340/521 |
| 2009/0197229 | A1 * | 8/2009 | Blackburn | G09B 19/00 434/226 |
| 2009/0263770 | A1 * | 10/2009 | Ambrose | G09B 9/00 434/218 |
| 2012/0132814 | A1 * | 5/2012 | Weinberg | G01V 5/0075 250/362 |
| 2012/0197896 | A1 * | 8/2012 | Li | H04L 29/08072 707/740 |
| 2013/0189658 | A1 * | 7/2013 | Peters | G09B 5/00 434/234 |
| 2013/0295538 | A1 * | 11/2013 | Ambrose | G09B 9/00 434/218 |
| 2015/0090456 | A1 * | 4/2015 | Turkenburg | G01V 9/00 166/305.1 |

OTHER PUBLICATIONS

Howard et al. ("Mobile Sensor Network Deployment using Potential Fields: A Distributed, Scalable Solution to the Area Coverage Problem", DARS02, 2002, pp. 1-11).*

Cui et al. ("Swarm-based Fuzzy Logic Control Mobile Sensor Network for Hazardous Contaminants Localization", 2004, IEEE, pp. 194-203) (Year: 2004).*

Howard et al. ("Mobile Sensor Network Deployment using Potential Fields: A Distributed, Scalable Solution to the Area Coverage Problem", 2002, DARS02, pp. 1-11) (Year: 2002).*

Ligon et al. ("Simulation of the passive infrared spectral signatures of bioaerosol and natural fog clouds immersed in the background atmosphere", 2012, Optical Society of America, pp. 1-12) (Year: 2012).*

International Search Report and Written Opinion for PCT/US2014/037210, dated Jan. 15, 2015.

European Supplemental Partial Search Report for EP14854212.9, dated Mar. 23, 2017.

* cited by examiner

INJECTION OF SIMULATED SOURCES IN A SYSTEM OF NETWORKED SENSORS

CROSS-REFERENCE TO RELATED APPLICATIONS

This application is the U.S. national stage of international application Ser. No. PCT/US2014/037210, entitled "INJECTION OF SIMULATED SOURCES IN A SYSTEM OF NETWORKED SENSORS," filed May 7, 2014, which claims benefit of and priority to U.S. Provisional Ser. No. 61/891,636, entitled "INJECTION OF SIMULATED SOURCES IN A SYSTEM OF NETWORKED SENSORS," filed Oct. 16, 2013 by Daniel A. Cooper, James B. Costales, Krzysztof Kamieniecki, Robert J. Ledoux, and Jeffrey K. Thompson, both of which are hereby incorporated herein by reference in their entirety.

BACKGROUND

Law enforcement and other agencies use a variety of sensors to detect hazardous materials such as radioactive/nuclear materials, chemicals, biohazards and explosives. Training and testing personnel and equipment with actual hazardous material presents problems. For example, radioactive sources that are dangerous enough to realistically portray a potential terrorist or environmental hazard will also be potentially hazardous to trainees, and may present a safety risk to the public. It may also be difficult, for reasons of cost, security, regulations, etc., to maintain an actual inventory of all potentially threatening sources merely for training purposes.

Simulated sources solve many such problems. A simulated source injected into a detection system can be made indistinguishable from a real source, from the point of view of sensor nodes and trainees, providing realistic training and systems testing. A simulated source has no associated radioactive or other hazards since there is no actual source involved. And the only practical limit on the diversity of simulated training scenarios is the imagination of the programmer responsible for the simulation. Unusual or unexpected situations are just as easy to simulate as run-of-the-mill hazards and do not require stockpiling of exotic materials.

Simulated sources can be used both to train users and also to test the system.

SUMMARY

Simulated sources can be injected into a networked system for use in training and/or testing.

DETAILED DESCRIPTION

The presence of a source can be detected using a network of sensors. A group of people, e.g., security personnel, first responders, etc., may patrol an area, each carrying or wearing a detector that is connected to a network, in some cases wirelessly. Sensors may also be fixed in place, for example at a security checkpoint or other significant location. Sensors may also be mounted on vehicles, for example, vehicles for used in public transportation, vehicles used by the general public, or vehicles used by first responders or other security or patrol personnel, such as cars, trucks, boats or aircraft. The detector may be a radiation detector, a chemical detector, or any other suitable detector for the source in question. In normal operation each networked sensor collects data that may be transmitted to a central processor or other nodes in the network, and the sensor may in turn receive such signals, with the result that data from the network as a whole is collectively processed to determine if, when, and where a source is present.

In a simulation mode which could be used for testing or training, the presence of a source can be simulated. The properties of the simulated source such as location, velocity, and activity level, are predetermined. Those properties are then combined with the known properties of each sensor node, such as location, velocity and sensitivity, to calculate an estimate what each sensor's response would be if the simulated source were real. Other simulated source properties may be included as well, for example, orientation and directional emission characteristics, or a spectral characteristic such as emission according to the spectrum of a particular radioisotope. The estimated response can be treated, for training or testing purposes, as if it were the actual response of the detector to a real source. This can be accomplished in one, or a combination, of three ways.

Figure 1:
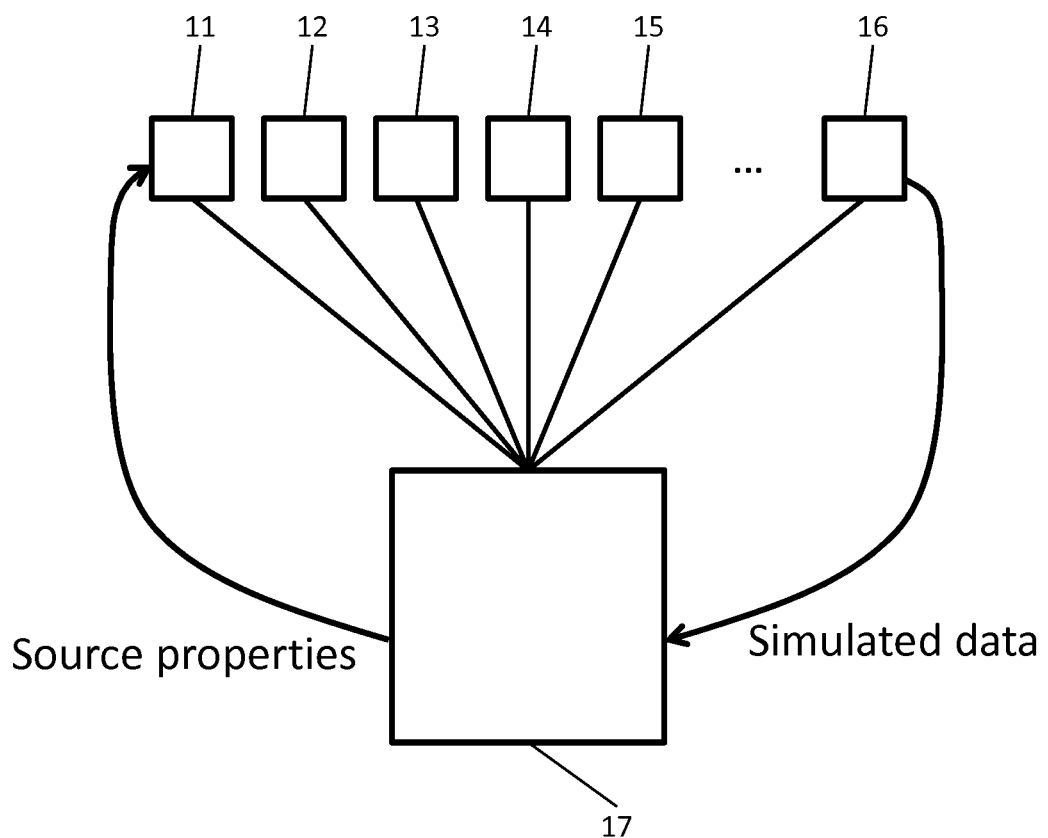
FIGS. 1-3 schematically show a sensor network in which a simulated source or sources are used for training or testing.

In a first alternative, shown schematically in FIG. 1, the simulated source properties could be transmitted to each sensor node 11-16 where each node would individually estimate its hypothetical response, resulting in simulated data. That simulated data would then be treated by the sensor node in the same way that actual data would in an actual deployment of the system, by transmitting the data across the network for collective analysis. The collective analysis could be carried out by a central processor 17, or in some other way over the network. This method requires each sensor node to maintain the necessary information about its own state to be able to estimate its response to an arbitrary source. Such information might include location, velocity, sensitivity, and could also include a description of its physical surroundings, either empirical or simulated, for example a map of background radiation, or the locations of significant geographical features like buildings or bodies of water. In some embodiments the node can also sense and report on other aspects of its local environment, such as ambient temperature, humidity, and/or barometric pressure, the lack or presence of precipitation, amount and/or type of precipitation, and wind speed and/or direction.

Figure 2:
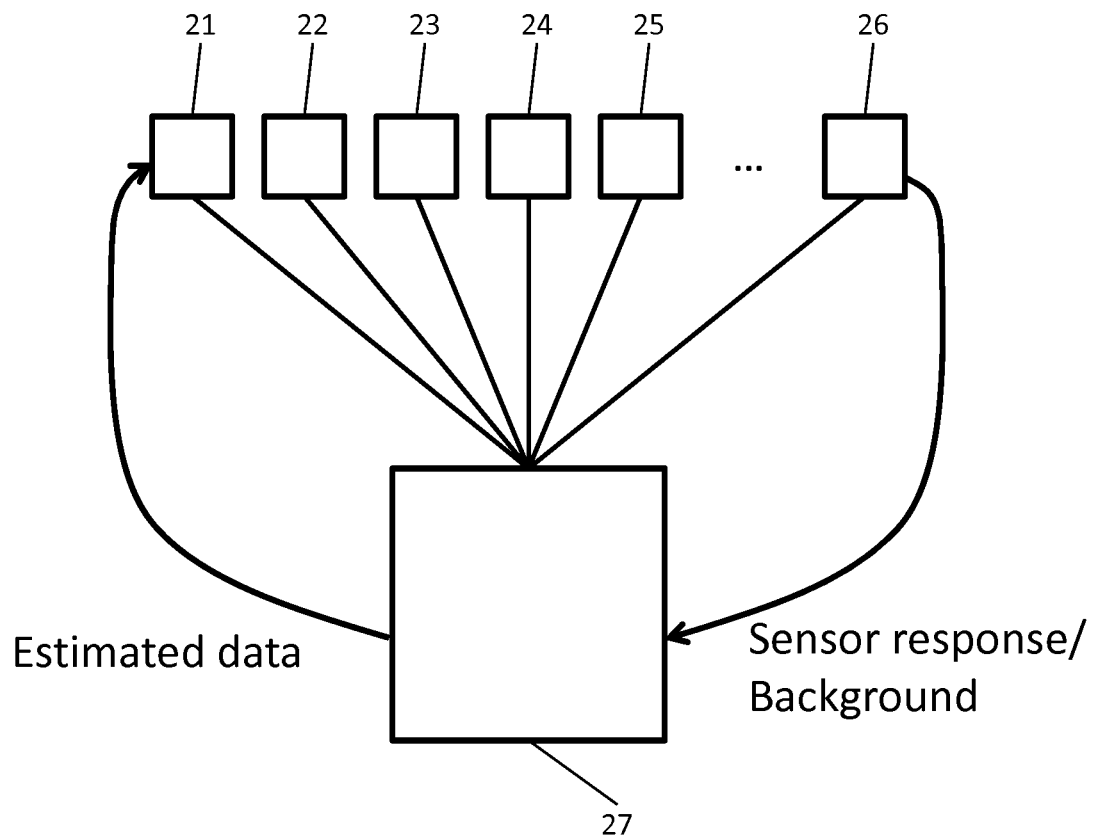

In a second alternative, shown schematically in FIG. 2, a central processor 27 would store information about the simulated source, and collect information about the state of each sensor 21-26, such as sensor location, sensor velocity and sensor sensitivity. The central processor 27 would then calculate for each sensor 21-26 an estimate of the sensor's response to the simulated source. The central processor 27 could likewise store additional information, either empirical or simulated, on background radiation or significant geography that could be used to construct a physical model which in turn could be included in the estimate of each sensor's response to the simulated source. The simulated data could then be sent back to each sensor node for high level processing, e.g., in systems where each node is separately responsible for triggering alarms, or reporting data to its user. Although the additional information used by the central processor could be the same sort of information used by each individual node in the first alternative, the second alternative may allow for the use of more complex information and physical models, since a central processor can have more computing power than a portable sensor node.

Figure 3:
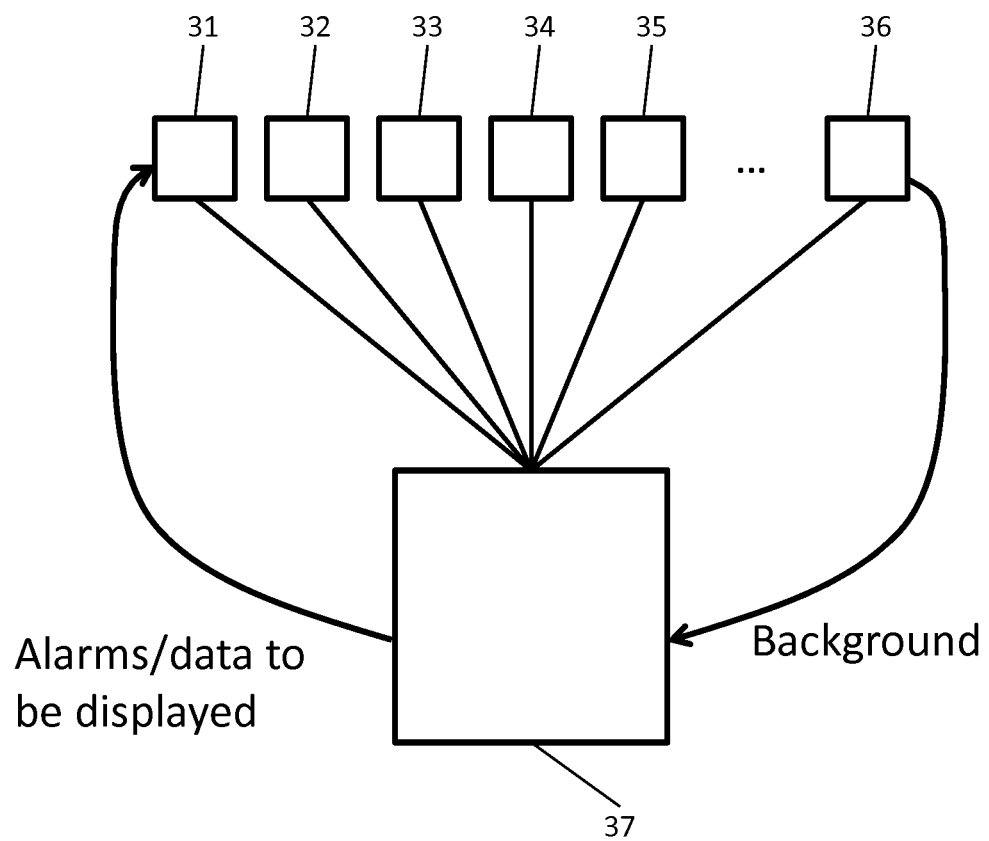

In a third alternative, shown schematically in FIG. 3, all calculation and processing would be carried out by a central processor 37, including high-level calculations. Individual nodes 31-36 would simply receive from the central processor any data to be displayed or alarm indications to be communicated to the user. In this case, the nodes need not be fully functioning sensor nodes, and could instead be training nodes capable only of receiving instructions regarding what to display through a user interface, i.e., "dumb" nodes. Or in this alternative the sensor nodes could contribute actual measurements of background to the central processor and function as more than "dumb" training nodes. Indeed, in all three alternatives, the individual nodes can either continually measure and record background radiation and contribute that data to the simulation, or simply rely on a simulated background.

In each of the three alternatives, the simulated source properties can be based on a purely virtual source whose properties are based on no real world data, or the simulated source location as a function of time can be based on the location of a "prey" node. Just like the other nodes, the prey node can report its position back to the central processor as a function of time. The central processor could then use the prey node's location as a predetermined location of the simulated source at each time. The prey node could be carried by training personnel who could add to the training scenario, for example, by moving to evade trainees carrying sensor nodes.

In all cases, an advantage of the systems and methods described herein is that the simulated signal is injected into a live network, in many cases including live data being collected and analyzed in real-time. The simulated source could be the only data, simulated or real, in the system. Or the simulated source could be injected into the system along with injected, simulated background measurements, for example, in order to test the detection power of a system as a function of signal to noise ratio. Or the simulated source could be injected over actual data being acquired in real time. This last alternative allows for a realistic training and/or testing environment, referred to as "sim-over-live." By injecting a simulated source over real background data, a system can avoid computationally expensive simulation of background radiation, while simultaneously making the simulation realistic. Such an injected source can be included with or without alerting users that a simulation is going on. That has the advantage of making the test more realistic. Another benefit is avoiding downtime; during such a test, the system could continue to operate normally at the same time, continuing to potentially detect real sources during the simulation.

In all embodiments described herein, any simulation can be carried out with a plurality of simulated sources, or a single simulated source.

In addition to training users, injection of sources can be useful both for testing the operation of a system of nodes, e.g., systems integration of the various parts of the network, and also for empirically testing the sensitivity of the system as a whole. A simulated source can be injected into a working system in order to see whether, in a real-life situation, a given type of source would be detected by the system. This can provide insight into how many sensors are required for a particular threat scenario or to test new CONOPs in operationally realistic scenarios.

In all embodiments there are at least two basic functions of the processing, (1) normal processing of data that would be used in normal operation to detect a source or sources, and (2) managing testing/training data and other signals and their movement through and use in the network. These two functions can be performed in a single processor 17, 27, 37 or split over separated elements of the system. A central processor can have many additional functions as well, including situational awareness of a testing/training exercise, and evaluation and feedback on the exercise.

In any of these embodiments, the central processor can, at each time step, store the locations and simulated responses of each node. This allows for after-the-fact analysis of the response of the system and its users, e.g., a playback of the simulation.

Examples of Certain Embodiments

A method can simulate the response of a system to at least one simulated source, the at least one simulated source having at least a predetermined simulated source location and a predetermined simulated source activity level at a predetermined time. The system can include a plurality of nodes; a central processor programmed to determine whether a source is detected by applying a predetermined algorithm to data associated with the plurality of nodes, the central processor having stored within it the predetermined simulated source location and the predetermined simulated source activity level; a network linking each node and the central processor such that signals can be transmitted between each node and the central processor; and an output device.

The method can include: (1) transmitting through the network from each node to the central processor a measured or inferred location for that node at the predetermined time; (2) calculating, based on at least (a) the measured or inferred location of each node at the predetermined time, (b) the predetermined simulated source location at the predetermined time, and (c) the predetermined simulated source activity level at the predetermined time, simulated response data for each node associated with the predetermined time; (3) in the central processor, applying the predetermined algorithm to the simulated response data for all the nodes, thereby determining whether a real source at the predetermined simulated source location having the predetermined simulated source activity level would have been detected at the predetermined time; and (4) signaling with the output device whether a real source at the predetermined simulated source location having the predetermined simulated source activity level would have been detected at the predetermined time.

In some such methods step (2) can be carried out in the central processor; and in step (2), calculating simulated response data for each node can be further based on simulated background data for each node. The simulated background data for each node can be generated by the central processor based on (a) the measured or inferred location of each node and (b) a predetermined background model stored in the central processor.

In some such methods each of, or some of, the plurality of nodes can include a sensor. In such methods, step (1) can further include transmitting through the network from each node to the central processor background data measured with that node's sensor; step (2) can be carried out in the central processor; and in step (2), calculating simulated response data for each node can be further based upon the transmitted background data measured with that sensor. In such methods, each of the plurality of nodes can further includes a node processor; in step (2), calculating simulated response data for each node can be carried out in that node's processor; and in step (2), calculating simulated response data for each node can be further based upon background data measured with that node's sensor. A sensor on a node can be, for example, a radiation detector or a chemical detector.

In some such methods the at least one simulated source can have at least predetermined simulated source locations and a predetermined simulated source activity levels at each of a plurality of predetermined times. Such methods can further include repeating steps (1)-(4) at each of the plurality of predetermined times.

In some such methods the at least one simulated source further can have a predetermined simulated source trajectory including the predetermined simulated source location and a predetermined simulated source velocity at each predetermined time; step (1) can further include transmitting across the network from each node to the central processor a measured or inferred velocity for each node at the predetermined time; and in step (2), calculating simulated response data for each node can further be based on the predetermined simulated source trajectory and velocity of that node at the predetermined time. The trajectory can be simple, such as for a stationary source, or more complex, such as a simulated trajectory of a pedestrian, or a vehicle.

Each node may be identical or substantially identical. Or the system may include nodes with a variety of different characteristics. One or more nodes may be located on a person. One or more nodes may be stationary, for example, a permanently installed node in a public place such as a signpost or lamppost. The output device may be located on one or more of the nodes, and/or on the central processor. Each node may include its own output device. If so, step (4) can further include signaling with (a) the output device included in the node closest to the predetermined simulated source location and/or (b) any other output devices included in nodes within a predetermined distance from the predetermined simulated source location.

In some such methods the at least one simulated source further has a predetermined simulated source spectral characteristic. In such methods, in step (2), calculating simulated response data for each node can be further based on the predetermined simulated source spectral characteristic.

In some such methods, step (1) can also include transmitting through the network from each node to the central processor a measured or inferred orientation for that node at the predetermined time. In such methods, in step (2), calculating simulated response data for each node can be further based on the measured or inferred orientation for that node at the predetermined time.

In some such methods, step (1) can also include transmitting through the network from each node to the central processor at least one measured or inferred environmental condition. In such methods, in step (2), calculating simulated response data for each node can be further based on the transmitted at least one measured or inferred environmental condition for that node. Such environmental conditions can include for example, (a) rate, amount or type of precipitation, (b) wind speed and/or wind direction, (c) ambient temperature, e.g., air or water temperature, (d) humidity, and (e) barometric pressure.

Some such methods can also include (5) storing at the predetermined time, the simulated response data for each node associated with the predetermined time and data representative of whether a real source at the predetermined simulated source location having the predetermined simulated source activity level would have been detected at the predetermined time. Such methods may also include repeating step (5) at each of the plurality of predetermined times.

In such methods storing can include storing data in either (a) the central processor, or (b) one or more nodes, or both (a) and (b).

In some such methods the at least one simulated source can be a plurality of simulated sources.

In some such methods the predetermined simulated source location can be a location in a two or three dimensional coordinate system.

In some such methods, one of the plurality of nodes is a designated prey node. In such methods, the predetermined simulated source location at the predetermined time can be based on the measured or inferred location of the prey node at the predetermined time.

In some embodiments, a method of simulating the response of a system to a simulated source can include providing a system including (a) a plurality of sensors and (b) a central processor having an output device; formulating, in the central processor, a simulated source; estimating the response of each of the plurality of sensors to the simulated source; and outputting from the output device a signal indicative of whether the system would be able to detect a real source having the properties of the simulated source.

While the systems and methods disclosed herein have been particularly shown and described with references to exemplary embodiments thereof, they are not so limited and it will be understood by those skilled in the art that various changes in form and details may be made therein without departing from the scope of the disclosure. It should be realized this invention is also capable of a wide variety of further and other embodiments within the scope of the invention. Those skilled in the art will recognize or be able to ascertain using no more than routine experimentation, many equivalents to the exemplary embodiments described specifically herein. Such equivalents are intended to be encompassed in the scope of the present disclosure.

We claim:

1. A computer-implemented method of determining a response of a detection system capable of detecting a real source to a simulated source, the detection system comprising a set of nodes connected in a network and located in a given area, each node including at least one sensor capable of sensing the real source, the method comprising the steps of:
    (a) operating the set of nodes to at least measure real background data using the at least one sensor of each node in the given area;
    (b) receiving at a processor in the network from a plurality of said nodes over the network measured or inferred location data for each node and the real background data measured by each node at a predetermined time in the given area;
    (c) receiving at the processor an injection of simulated source data including data on a location of the simulated source and an activity level of the simulated source at the predetermined time;
    (d) calculating, by the processor, estimated simulated response data for each node at the predetermined time based at least on the measured or inferred location data received from each node and the real background data measured by the node at the predetermined time received at step (b) and the simulated source data received at step (c);
    (e) determining, by the processor, based on the estimated simulated response data for all the nodes whether a real source at the predetermined simulated source location having the predetermined simulated source activity level would have been detected at the predetermined time; and (f) signaling with an output device whether a real source at the predetermined simulated source location having the predetermined simulated source activity level would have been detected at the predetermined time, wherein the simulated source has a predetermined simulated source spectral characteristic comprising an emission spectrum of predetermined isotope, and step (d) comprises calculating the estimated simulated response data for each node based in part on the predetermined simulated source spectral characteristic.

2. The method of claim 1, further comprising transmitting the estimated simulated response data calculated in step (d) for each node to that node over the network for further processing by the node.

3. The method of claim 2, wherein the further processing by the nodes comprises triggering an alarm or reporting data to a user of the node.

4. The method of claim 1, wherein the processor comprises a centralized computer processor connected by the network to each of said nodes.

5. The method of claim 1, wherein step (a) further comprises operating the nodes to simultaneously detect a real source.

6. The method of claim 1, wherein determining a response of a detection system to the simulated source is performed without alerting users operating the nodes.

7. The method of claim 1, wherein the background data comprises background radiation data.

8. The method of claim 1, wherein the sensors are either radiation detectors or chemical detectors.

9. The method of claim 1, wherein steps (a) to (f) are repeatedly performed a plurality of times.

10. The method of claim 1, wherein at least one of said nodes is stationary and at least one of said nodes is mobile.

11. The method of claim 1, wherein step (b) further comprises receiving from a plurality of said nodes over the network measured or inferred orientation data for each node at the predetermined time, and step (d) comprises calculating estimated simulated response data for each node based in part on the measured or inferred orientation for that node at the predetermined time.

12. The method of claim 1, further comprising designating one of the plurality of nodes as a designated prey node, and wherein the simulated source location at the predetermined time comprises the measured or inferred location of the prey node at the predetermined time.

13. The method of claim 1, wherein step (b) further comprises receiving at the processor from the plurality of said nodes at least one measured or inferred environmental condition; and wherein step (d) comprises calculating the estimated simulated response data for each node at the predetermined time based in part on the measured or inferred environmental condition for that node.

14. The method of claim 13, wherein the at least one environmental condition is at least one of (a) rate, amount, or type of precipitation, (b) wind speed and/or wind direction, (c) ambient temperature, (d) humidity, and (e) barometric pressure.

15. A detection system capable of detecting a real source, comprising:

a plurality of nodes located in a given area, each node including at least one sensor capable of at least measuring real background data and sensing the real source in the given area;

a processor connected to each of the plurality of nodes over a communications network, said processor configured to:

(a) receive from a plurality of said nodes over the network measured or inferred location data for each node and the real background data measured by each node at a predetermined time in the given area;

(b) receive an injection of simulated source data including data on a location of a simulated source and an activity level of the simulated source at the predetermined time;

(c) calculate estimated simulated response data for each node at the predetermined time based at least on the measured or inferred location data received from each node and the real background data measured by the node at the predetermined time and the simulated source data;

(d) determine based on the estimated simulated response data for all the nodes whether a real source at the predetermined simulated source location having the predetermined simulated source activity level would have been detected at the predetermined time; and (e) signal with an output device whether a real source at the predetermined simulated source location having the predetermined simulated source activity level would have been detected at the predetermined time, wherein the simulated source has a predetermined simulated source spectral characteristic comprising an emission spectrum of predetermined isotope, and step (c) comprises calculating the estimated simulated response data for each node based in part on the predetermined simulated source spectral characteristic.

16. The system of claim 15, wherein the processor comprises a centralized computer processor connected by the network to each of said nodes.

17. The system of claim 15, wherein at least one of said nodes is stationary and at least one of said nodes is mobile.

18. The system of claim 15, wherein one of the plurality of nodes is a designated prey node, and wherein the simulated source location at the predetermined time comprises the measured or inferred location of the prey node at the predetermined time.

19. A computer-implemented method of determining a response of a detection system capable of detecting a real source to a simulated source, the detection system comprising a set of nodes connected in a network and located in a given area, each node including at least one sensor capable of sensing the real source, the method comprising the steps of:

(a) operating the set of nodes to at least measure real background data using the at least one sensor of each node in the given area;

(b) receiving at a processor in the network from a plurality of said nodes over the network measured or inferred location data for each node and the real background data measured by each node at a predetermined time in the given area;

(c) receiving at the processor an injection of simulated source data including data on a location of the simulated source and an activity level of the simulated source at the predetermined time;

(d) calculating, by the processor, estimated simulated response data for each node at the predetermined time based at least on the measured or inferred location data received from each node and the real background data measured by the node at the predetermined time received at step (b) and the simulated source data received at step (c);

(e) determining, by the processor, based on the estimated simulated response data for all the nodes whether a real source at the predetermined simulated source location having the predetermined simulated source activity level would have been detected at the predetermined time; and (f) signaling with an output device whether a real source at the predetermined simulated source location having the predetermined simulated source activity level would have been detected at the predetermined time, wherein the simulated source has a predetermined directional emission characteristic, and step (d) comprises calculating the estimated simulated response data for each node based in part on the predetermined directional emission characteristic.

20. The method of claim 19, further comprising transmitting the estimated simulated response data calculated in step (d) for each node to that node over the network for further processing by the node.

21. The method of claim 20, wherein the further processing by the nodes comprises triggering an alarm or reporting data to a user of the node.

22. The method of claim 19, wherein the processor comprises a centralized computer processor connected by the network to each of said nodes.

23. The method of claim 19, wherein step (a) further comprises operating the nodes to simultaneously detect a real source.

24. The method of claim 19, wherein determining a response of a detection system to the simulated source is performed without alerting users operating the nodes.

25. The method of claim 19, wherein the background data comprises background radiation data.

26. The method of claim 19, wherein the sensors are either radiation detectors or chemical detectors.

27. The method of claim 19, wherein steps (a) to (f) are repeatedly performed a plurality of times.

28. The method of claim 19, wherein at least one of said nodes is stationary and at least one of said nodes is mobile.

29. The method of claim 19, wherein step (b) further comprises receiving from a plurality of said nodes over the network measured or inferred orientation data for each node at the predetermined time, and step (d) comprises calculating estimated simulated response data for each node based in part on the measured or inferred orientation for that node at the predetermined time.

30. The method of claim 19, further comprising designating one of the plurality of nodes as a designated prey node, and wherein the simulated source location at the predetermined time comprises the measured or inferred location of the prey node at the predetermined time.

31. The method of claim 19, wherein step (b) further comprises receiving at the processor from the plurality of said nodes at least one measured or inferred environmental condition; and wherein step (d) comprises calculating the estimated simulated response data for each node at the predetermined time based in part on the measured or inferred environmental condition for that node.

32. The method of claim 31, wherein the at least one environmental condition is at least one of (a) rate, amount, or type of precipitation, (b) wind speed and/or wind direction, (c) ambient temperature, (d) humidity, and (e) barometric pressure.

33. A detection system capable of detecting a real source, comprising:
   a plurality of nodes located in a given area, each node including at least one sensor capable of at least measuring real background data and sensing the real source in the given area;
   a processor connected to each of the plurality of nodes over a communications network, said processor configured to:
   (a) receive from a plurality of said nodes over the network measured or inferred location data for each node and the real background data measured by each node at a predetermined time in the given area;
   (b) receive an injection of simulated source data including data on a location of a simulated source and an activity level of the simulated source at the predetermined time;
   (c) calculate estimated simulated response data for each node at the predetermined time based at least on the measured or inferred location data received from each node and the real background data measured by the node at the predetermined time and the simulated source data;
   (d) determine based on the estimated simulated response data for all the nodes whether a real source at the predetermined simulated source location having the predetermined simulated source activity level would have been detected at the predetermined time; and
   (e) signal with an output device whether a real source at the predetermined simulated source location having the predetermined simulated source activity level would have been detected at the predetermined time,
   wherein the simulated source has a predetermined directional emission characteristic, and step (c) comprises calculating the estimated simulated response data for each node based in part on the predetermined directional emission characteristic.

34. The system of claim 33, wherein the processor comprises a centralized computer processor connected by the network to each of said nodes.

35. The system of claim 33, wherein at least one of said nodes is stationary and at least one of said nodes is mobile.

36. The system of claim 33, where in one of the plurality of nodes is a designated prey node, and wherein the simulated source location at the predetermined time comprises the measured or inferred location of the prey node at the predetermined time.

* * * * *